United States Patent [19]

Dönges et al.

[11] Patent Number: 5,554,768

[45] Date of Patent: Sep. 10, 1996

[54] SUBSTITUTED SUCCINIMIDES

[75] Inventors: Reinhard Dönges, Bad Soden; Rudolf Ehrler, Flörsheim; Rainer Helwerth, Eschborn, all of Germany

[73] Assignee: Hoechst Aktiengesellschaft, Germany

[21] Appl. No.: 248,764

[22] Filed: May 25, 1994

[30] Foreign Application Priority Data

May 27, 1993 [DE] Germany .................. 43 17 651.8

[51] Int. Cl.$^6$ ................ C07D 207/408; C07D 207/325; C07D 207/404; C07D 207/412
[52] U.S. Cl. .................... 548/545; 548/531; 548/536; 548/544; 548/550
[58] Field of Search .................... 548/545, 531, 548/536, 544, 550

[56] References Cited

U.S. PATENT DOCUMENTS

| | | | |
|---|---|---|---|
| 3,184,474 | 5/1965 | Catto et al. | 260/326.3 |
| 3,272,746 | 9/1966 | Le Suer et al. | 252/47.5 |
| 3,324,033 | 6/1967 | Knapp | 252/51.5 |
| 4,102,798 | 7/1978 | Ryer et al. | 252/51.5 A |

OTHER PUBLICATIONS

"Reactions of D–Mannitol Carbonate Derivatives Catalyzed by Tetraethylammonium Bromide", Carbohydrate Research, 52 (1976) pp. 50–61. Elsevice Scientific Publishing Company, Amsterdam.
Prisadki Smaz. Maslam Bd. 5, 1978 Seiten 133–137 Z. E. Aliev et al. "Studies of the effect of some organic compounds on antifouling and anticorrosion properties of heavy fuels".
Azerb. Khim. Zh., Nr. 2, 1986 Seiten 119–122, A. B. Abdinova et al. "Inhibition activity of unsaturated nitrogen–containing hydroxyethers".
Ishido et al, Carbohydrate Research, vol. 52 (1976) pp. 49–61.
EP94107839 Oct. 1994 Germany Search Report Therefor.

Primary Examiner—David B. Springer
Attorney, Agent, or Firm—Connolly & Hutz

[57] ABSTRACT

The present invention relates to succinimides of the formula I

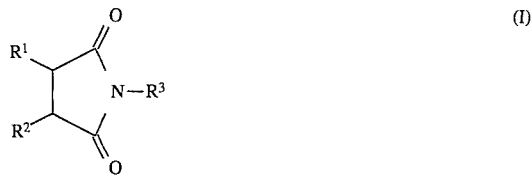

in which $R^1$ and $R^2$, independently of one another, are hydrogen, $C_1$-$C_{24}$-alkyl, $C_2$-$C_{24}$-alkenyl, $C_6$-$C_{12}$-cycloalkyl, $C_6$-$C_{12}$-cycloalkenyl, $C_6$-$C_{12}$-aryl, $C_1$-$C_{24}$-alkoxy, $C_1$-$C_{24}$-acyl, $C_1$-$C_{24}$-acyloxy, a hydroxyl, amino or sulfo group or a $C_1$-$C_{24}$-dialkylamino, $C_1$-$C_{24}$-acylamino, $C_1$-$C_{24}$-alkylsulfato, $C_1$-$C_{24}$-alkylsulfonato, $C_1$-$C_{24}$-alkylsulfito, $C_1$-$C_{24}$-alkylsulfinyl or $C_1$-$C_{24}$-alkoxycarbonyl radical, and $R^3$ is a polyhydroxyalkyl radical of the formula

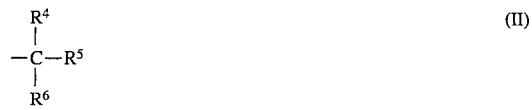

in which $R^4$ is —(CHOR$^7$)$_n$—H, $R^5$ is —(CHOR$^7$)$_m$—H, $R^6$ is —(CHOR$^7$)$_o$—H where n+m+o is 2–6, and $R^7$ is H or a carbohydrate attached in the form of a glycoside from the series comprising reducing sugars, a process for their preparation and their use.

11 Claims, No Drawings

SUBSTITUTED SUCCINIMIDES

DESCRIPTION

Nonionic surfactants (see H. Bueren, H. Großmann; Grenzflächenaktive Substanzen p. 83 ff., Verlag Chemie 1971) are present in almost all of today's detergents and cleaning agents. They are distinguished in particular by good skin compatibility and stability to water hardness. Of the nonionic surfactants, polyalkylene oxide derivatives have achieved the greatest importance in terms of economics. They are obtained by subjecting alkylene oxides, such as ethylene oxide or propylene oxide, to an addition reaction with fatty alcohols, fatty amines, carboxylic acids or carboxamides. The hydrophilic portion of the surfactant is a polyether chain. The hydrophilicity of the surfactant can be adjusted within wide limits via the number of ether molecules which have undergone addition. A disadvantage with the large-scale production of these compounds is the high toxicity and the high potential hazard of the raw materials, in particular of ethylene oxide, as a result of which extensive safety precautions have to be employed during production.

Amine oxides, sulfoxides and phosphine oxides containing long-chain alkyl radicals have likewise been described as nonionic surfactants. In these compounds, the strongly dipolar character of the heteroatom-oxygen bond constitutes the hydrophilic center. However, as surfactants, they are of little economic importance.

A further large field in the nonionic surfactant sector are the compounds whose hydrophilic portion is formed by carbohydrates (see G. Gawalek, Tenside, Akademie-Verlag Berlin 1975, p. 274 ff.). Of these, alkyl oligoglucosides, which can be prepared from the readily available raw materials fatty alcohol and glucose or starch, are of great economic interest. Like most carbohydrate surfactants, they are regarded as being particularly kind to skin and readily biodegradable. The commercially available alkyl oligoglucosides are obtained by Fischer glycosidation or by transglycosidation of short-chain alkyl glycosides with fatty alcohols. As a result of preparation, they comprise mixtures of various short-chain oligoglucosides.

The longest-known carbohydrate surfactants include sugar esters. They are obtained by transesterification of fatty acid methyl esters with carbohydrates, typically sucrose (Snell et al. Ind. Eng. Chem. 48, 1459 (1956)).

Condensation of fatty acids with alditols, such as sorbitol, gives, depending on the conditions, alditol esters (GB-A-872,507), anhydroalditol esters and dianhydro-alditol esters (U.S. Pat. No. 2,322,820). However, the application range of ester-based nonionic surfactants is in general severely limited by the ease of hydrolysis of the ester group.

Condensation of alkylglycamines and fatty acids to give N-acylglycamines in which the sugar radical is attached to the fatty acid via an amino group forms the subject-matter of U.S. Pat. No. 1,985,424. These long-chain polyhydroxy amides are used as textile auxiliaries.

If higher temperatures are used during condensation, the corresponding anhydro- and dianhydroglycamides (U.S. Pat. No. 2,993,887) are formed with elimination of water. They too are described as being detergent-active.

U.S. Pat. No. 3,018,247, U.S. Pat. No. 3,018,250 and U.S. Pat. No. 3,018,291 disclose alkenylsuccinimides which are obtained by reaction of alkenylsuccinic acid or its anhydride with a polyamine (e.g. tetraethylenepentamine) and their use as dispersants for lubricating oils.

U.S. Pat. No. 4,102,798 describes the reaction of alkenylsuccinic anhydrides with monosubstituted 2-aminoethanols.

U.S. Pat. No. 3,184,474 mentions reaction products of alkenylsuccinic acids and anhydrides thereof with a mixture of polyhydric alcohols (e.g. glycols, amino alcohols) and polyamines (e.g. dimethylaminomethylamine, tetrapropylenepentamine) and their use as anticorrosives in lubricating oils.

On the basis of the prior art described above, the object of the present invention is to provide succinimides based on primary sugar amines.

The invention accordingly provides succinimides of the formula I

in which $R^1$ and $R^2$, independently of one another, are hydrogen, $C_1$-$C_{24}$-alkyl, $C_2$-$C_{24}$-alkenyl, $C_6$-$C_{12}$-cycloalkyl, $C_6$-$C_{12}$-cycloalkenyl, $C_6$-$C_{12}$-aryl, $C_1$-$C_{24}$-alkoxy, $C_1$-$C_{24}$-acyl, $C_1$-$C_{24}$-acyloxy, a hydroxyl, amino or sulfo group or a $C_1$-$C_{24}$-dialkylamino, $C_1$-$C_{24}$-acylamino, $C_1$-$C_{24}$-alkylsulfato, $C_1$-$C_{24}$-alkylsulfonato, $C_1$-$C_{24}$-alkylsulfito, $C_1$-$C_{24}$-alkylsulfinyl or $C_1$-$C_{24}$-alkoxycarbonyl radical, and $R^3$ is a polyhydroxyalkyl radical of the formula

in which $R^4$ is —(CHOR$^7$)$_n$—H, $R^5$ is —(CHOR$^7$)$_m$—H, $R^6$ is —(CHOR$^7$)$_o$—H where n+m+o is 2–6, and $R^7$ is H or a carbohydrate attached in the form of a glycoside from the series comprising reducing sugars.

The compounds of the formula I are obtained by reaction of carboxylic acids of the formula IIa and/or carboxylic anhydrides of the formula IIb

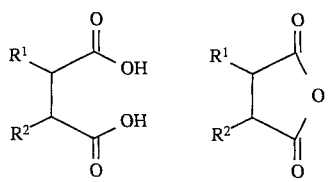

with amino compounds of the formula III

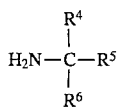

in which the radicals $R^1$, $R^2$, $R^3$, $R^4$, $R^5$ and $R^6$ have the abovementioned meanings.

Preferred compounds of the formula IIa/IIb are compounds in which $R^1$ and $R^2$ are hydrogen or $C_6$-cycloalkenyl, $R^1$ is hydrogen and $R^2$ is $C_1$-$C_{24}$-alkyl or $C_2$-$C_{24}$-alkenyl, $R^1$ is hydrogen and $R^2$ is a hydroxyl group, and $R^1$ is a $C_1-C_{24}$-acylamino radical and $R^2$ is hydrogen.

Examples include succinic anhydride, $C_1-C_{24}$-alkylsuccinic anhydride, $C_2-C_{24}$-alkenylsuccinic anhydride, $C_6$-cycloalkenylsuccinic anhydride and malic acid.

The compounds of the formula III are amino polyols which are usually obtained by reductive amination of the corresponding aldoses, ketoses, di- or oligosaccharides, in which context glucose, galactose, fructose, maltose, lactose and starch hydrolyzates are preferably used. A process for preparing amino polyols by reductive amination of aldoses in the presence of ammonia or hydrazine is described in U.S. Pat. No. 2,830,983. DE-A-3,625,931 mentions a process for the reductive amination of ketoses, di- and oligosaccharides. Further suitable amino polyols include compounds having a primary amino group and at least three hydroxyl groups, for example tris(hydroxyalkyl)aminomethane.

The invention also provides a process for preparing the succinimides of the formula I comprising the steps of introducing the amino polyol of the formula III into a suspending agent or solvent, adding the carboxylic anhydride IIa and/or carboxylic acid IIb, if appropriate with slight heating, and heating this mixture at a temperature and over a sufficiently long period to make the mixture substantially free of suspending agent or of solvent and the water of reaction formed and to bring the base nitrogen content of the reaction mixture down to less than 0.1% by weight.

Suitable suspending agents or solvents are water, alcohol or water/alcohol mixtures. Suitable alcohols are in particular lower aliphatic alcohols, such as methanol, ethanol, propanols, butanols and/or pentanols.

The preparation process according to the invention is illustrated by way of example with reference to the preparation of alkenylsuccinimides of the formula I. They can be synthesized starting from alkenylsuccinic anhydrides which can be prepared on a large industrial scale. These in turn are readily available by reacting olefins with maleic anhydride. The other starting materials required are the amino polyols described above.

The amino polyol is dissolved or suspended in water, a lower alcohol or a mixture thereof. Suitable solvents are in particular methanol and butanol. In the presence of water, addition of a tertiary amine is recommended as an auxiliary base. A particularly suitable base is triethylamine, since it can be easily distilled off together with the other solvents and reused in the next batch.

In the first reaction step, the alkenylsuccinic anhydride is added dropwise to the solution (or suspension) of the amino polyol at slightly elevated temperature, in general ranging from 20° to 80° C., preferably 50° to 70° C., to give the monoamide. Stirring is continued for a certain period of time, and removal of the solvent or suspending agent by distillation at elevated temperature is then started. The elevated temperature is in general 100° to 160° C. When no more solvent is present, the temperature is raised to at most 190° C., and the condensation reaction is carried out in the melt in a gentle stream of nitrogen with elimination of water to give the imide. The reaction is complete as soon as a sample of the reaction product dissolved in acetic acid and titrated with 0.1N perchloric acid shows a base nitrogen content of less than 0.1%. Formation of the succinimide can be detected by infrared spectroscopy. A strong band at about 1700 $cm^{-1}$ and a weaker one at about 1780 $cm^{-1}$ are characteristic of an imide structure. Provided solvents and auxiliary base are reused, the preparation does not give rise to any byproducts.

If starting with pure (distilled) alkenylsuccinic anhydrides, the succinimides prepared according to the invention can be isolated, in pure form, after crystallization. They can be characterized by $^1$H NMR, $^{13}$C NMR and high-pressure liquid chromatography (HPLC). As expected, condensation of a chiral, racemic alkenylsuccinic anhydride with an enantiomerically pure amino polyol, such as glucamine, gives a product mixture comprising two diastereomers in a ratio of about 1:1. This can be seen in the HPLC chromatograms and in part in the $^{13}$C NMR spectrum in the form of double peaks.

The compounds according to the invention are used in various areas of application and are suitable, for example, as detergent base materials. Moreover, these compounds can be stirred with water to give highly concentrated surfactant solutions which are readily handleable in industry. If required, the product can be bleached using hydrogen peroxide. In addition, these surfactant solutions, just like the succinimides according to the invention, have been found to be suitable as anticorrosives. In this application, it is customary to add 10–60% by weight of a nitrogen base, preferably tertiary amines, in particular trialkanolamines, relative to the weight of the solution, the pH of such aqueous solutions being greater than 7, preferably 8 to 12.

PREPARATION EXAMPLES

Example 1

Octenyl-N-(1-deoxyglucityl)succinimide

A 1 l 4-neck flask equipped with stirrer, reflux condenser, internal thermometer, dropping funnel and nitrogen inlet is charged with 90.5 g of glucamine in 300 ml of water-saturated butanol. 102.8 g of octenylsuccinic anhydride (technical grade) are added dropwise at an internal temperature of 60° C. over a period of 50 minutes. After stirring at 60° C. for another 60 minutes, the reflux condenser is replaced by a distillation head. Water/butanol is distilled off under a gentle stream of nitrogen. The flask temperature is increased to 150° C. After 3 hours, the base nitrogen content of the reaction product is no more than 0.2%. Cooling gives 167 g of the product.

Example 2

Tetrapropenyl-N-(1-deoxyglucityl)succinimide.

(Apparatus as in Example 1)

The flask is charged with 271.5 g of glucamine in 700 ml of water-saturated isobutanol. 443.4 g of tetrapropenylsuccinic anhydride (technical grade) are run in at an internal temperature of 60° C. over a period of 1 hour. Stirring at 60° C. is continued for 1 hour, and the solvents are then distilled off. The temperature of 160° C. (flask) reached at the end of the distillation process is maintained for another 2 hours. The melt is poured onto cold metal sheets and granulated after solidification. In the infrared spectrum, the product exhibits the characteristic imide bands at 1695 $cm^{-1}$ (very strong) and 1770 $cm^{-1}$ (weak). The acid number of the product is 20 mg of KOH/g, and the base nitrogen content 0.06%.

Example 3

Tripropenyl-N-(1-deoxyglucityl)succinimide (Apparatus and procedure as in Example 2)

386.3 g of tripropenylsuccinic anhydride (technical grade) are used.

Characteristic data of the product:

IR spectrum (KBr): 1695 cm$^{-1}$ (strong), 1770 cm$^{-1}$ (weak). Acid number: 22 mg of KOH/g. Base nitrogen: <0.1%.

Example 4

Dodecenyl-N-(1-deoxyglucityl)succinimide (Apparatus as in Example 1)

181 g of glucamine are suspended in 600 ml of water-saturated isobutanol and 101 g of triethylamine. 266 g of dodecenylsuccinic anhydride (technical grade, distilled) are added dropwise over a period of 1 hour. This gives a clear solution which is maintained at 60° C. for another hour. Isobutanol, water and triethylamine are distilled off at a bath temperature of 130° C., after which the temperature is raised to 165° C. Condensation is carried out under a gentle stream of nitrogen for 3 hours, during which additional small amounts of solvent and triethylamine distill off. The remaining base nitrogen content is no more than 0.09%. According to HPLC analysis, 85% of the crude product comprises the desired product. The cooled reaction batch is recrystallized from 400 ml of isopropanol to give 355.5 g (84% of theory) of colorless crystals having a melting point of 100°–105° C. The hydroxyl number is 652. This corresponds to a molecular weight of 430 (theory: 429).

$^1$H NMR spectrum (399.65 MHz, DMSO-d$_6$): δ=0.9–1.4 (17H, alkyl-H), 1.95–2.0 (4H, allyl-H), 2.28; 2.71 (2H each dd —CH$_2$—CO—), 2.84 (1H, R—CH—CO—), 3.2–3.7 (5H, —CHOH), 3.62; 3.85 (2H, N—CH$_2$), 4.3–4.8 (5H, —OH), 5.32; 5.50 (2H, —CH=CH—).

$^{13}$C NMR spectrum (100.4 MHz, DMSO-d$_6$): δ=13.88 (CH$_3$), 22.04–33.2 (—CH$_2$—, R—CHR—CO—, R—CH$_2$—CO—), 41.59 (N—CH$_2$—), 63.26 (—CH$_2$OH), 68.96–71.69 (—CHOH, 7 signals), 125.15; 125.7; 132.5; 133.4 (—CH=), 176.6; 176.7; 179.5; 179.6 (—CO—).

Critical micelle concentration (ring tensiometer 25° C.): 40 ppm.

Preparation of a surfactant solution:

Example 5

Dodecenyl-N-(1-deoxyglucityl)succinimide

A 1 l 4-necked flask equipped with stirrer, reflux condenser, internal thermometer, dropping funnel and nitrogen inlet is charged with 90.5 g of glucamine in 300 ml of water-saturated butanol. 133.0 g of dodecenylsuccinic anhydride (technical grade) are added dropwise at an internal temperature of 60° C. over a period of 1.5 hours. After stirring at 60° C. for another 30 minutes, the reflux condenser is replaced by a distillation head. Water/butanol is distilled off under a gentle stream of nitrogen. The flask temperature is raised to 185° C., and the temperature at the distillation head rises to 130° C. After reaching a flask temperature of 185° C., stirring at this temperature is continued for an hour, and the mixture is then cooled to 100° C. over a period of 1.5 hours. 140 g of water are added, and the batch is stirred until a homogeneous mixture is obtained. For bleaching, 5.0 g of a 35% by weight hydrogen peroxide solution are added at 90° C., and the resulting mixture is stirred for an hour to give a flowable surfactant concentrate (60.2%) which is readily water-miscible and has a low-temperature cloud point of −7° C.

Performance testing of the surfactant solution as detergent base material:

| Ross/Miles foaming power: | 220/220 at 0.1% of DAS |
|---|---|
| | 80/80 at 0.006% of DAS |

(DAS=detergent-active substance)

The colour of the surfactant solution is determined by the iodine color number. The iodine color number is 32 (at 40% of DAS).

Performance testing of the surfactant solution as anticorrosive:

167 g of octenyl-N-(1-deoxyglucityl)succinimide from Example 2 are stirred with 111 g of water until a homogeneous mixture is obtained. This gives a brown viscous surfactant concentrate having a solids content of 60%. 35 parts of this concentrate are mixed with 15 parts of fully deionized water and 50 parts of triethanolamine until a homogeneous mixture is obtained.

The solution is tested for anticorrosive properties by the method of DIN 51 360/II:

| c (in water of 20° German hardness) | Rating |
|---|---|
| 2% | 2 |
| 3% | 1 |
| 4% | 0 |
| 5% | 0 |

Example 6

N-(1-Deoxyglucityl)succinimide (glucimide of succinic acid).

Apparatus as Example 1.

The flask is charged with 90.5 g of glucamine in 300 ml of methanol. 50.0 g of succinic anhydride are introduced in portions at 50° C. under a nitrogen atmosphere. Stirring at 60° C. is continued for 1 hour, and the bath temperature is then slowly raised to 130° C. while distilling off the methanol. This results in a clear melt, which is heated at 165° C. in a nitrogen stream for another 3 hours with stirring. The crude product then has a base nitrogen content of 0.07%. It is dissolved in 100 ml of water while hot, and ethanol is added until the solution starts becoming cloudy. This gives 108 g of colorless crystals having a melting point of 176°–178° C., a hydroxyl number of 1032 mg/g (theory: 1077), base nitrogen 0.04%. IR bands at 1695 cm$^{-1}$ and 1775 cm$^{-1}$ (KBr) confirm the imide structure of the compound.

Example 7

N-(1-Deoxyglucityl)hydroxysuccinimide (glucimide of malic acid).

Apparatus as Example 1.

The flask is charged with 45.3 g of glucamine in 125 ml of methanol. 33.5 g of malic acid are added, and the mixture is refluxed for 3 hours. The reflux condenser is exchanged for a distillation head, and the methanol is completely distilled off. The residue is heated at 175° C. for 3 hours in a nitrogen stream. Cooling gives a brown, glassy product having a base nitrogen content of 0.1%. In the infrared spectrum, the absorption bands at 1700 cm$^{-1}$ and 1780 cm$^{-1}$ (film) show the presence of the imide.

What is claimed is:

1. A succinimide of the formula I

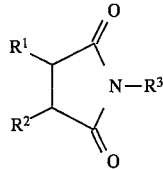

in which

R$^1$ and R$^2$, independently of one another, are hydrogen, C$_1$-C$_{24}$-alkyl, C$_2$-C$_{24}$-alkenyl, C$_6$-C$_{12}$-cycloalkyl, C$_6$-C$_{12}$-cycloalkenyl, C$_6$-C$_{12}$-aryl, C$_1$-C$_{24}$-alkoxy, C$_1$-C$_{24}$-acyl, C$_1$-C$_{24}$-acyloxy, a hydroxyl, amino or sulfo group or a C$_1$-C$_{24}$-dialkylamino, C$_1$-C$_{24}$-acylamino, C$_1$-C$_{24}$-alkylsulfato, C$_1$-C$_{24}$-alkylsulfonato, C$_1$-C$_{24}$-alkylsulfito, C$_1$-C$_{24}$-alkylsulfinyl or C$_1$-C$_{24}$-alkoxycarbonyl radical, and R$^3$ is a polyhydroxyalkyl radical of the formula

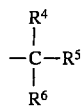

in which

R$^4$ is —(CHOR$^7$)$_n$—H,
R$^5$ is —(CHOR$^7$)$_m$—H,
R$^6$ is —(CHOR$^7$)$_o$—H where n+m+o is 2–6, and
R$^7$ is H.

2. A process for preparing a succinimide of the formula I, comprising the steps of introducing the amino polyol of the formula III

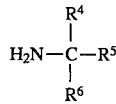

in which R$^3$, R$^4$ and R$^5$ have the meaning given in claim 1, into a suspending agent or solvent, adding the carboxylic acid IIa and/or the carboxylic anhydride IIb,

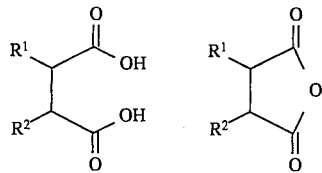

in which R$^1$ and R$^2$ have the meaning given in claim 1, if appropriate with slight heating, and heating this mixture at a temperature and over a sufficiently long period to make the mixture substantially free of suspending agent or of solvent and the water of reaction formed and to bring the base nitrogen content of the reaction mixture down to less than 0.1% by weight.

3. The process as claimed in claim 2, wherein the suspending agents or solvents used are water, alcohol, or a water/alcohol mixture.

4. The process as claimed in claim 2, wherein the addition takes place at a temperature of between 20° and 80° C.

5. The process as claimed in claim 2, wherein, in order to remove the suspending agent or solvent present, the mixture is heated to a maximum temperature of 160° C. and then, optionally, to a maximum temperature of 190° C.

6. The process as claimed in claim 2, wherein the mixture is heated over a period of up to 3 hours.

7. An aqueous solution, containing a succinimide of the formula I as claimed in claim 1.

8. An aqueous solution as claimed in claim 7, which contains 10–60% by weight of a nitrogen base, and has a pH of greater than 7.

9. The process as claimed in claim 3, wherein the alcohol is a lower aliphatic alcohol.

10. The process as claimed in claim 4, wherein the temperature is between 50° to 70° C.

11. An aqueous solution as claimed in claim 8, wherein said nitrogen base is a tertiary amine.

* * * * *